United States Patent
Tseng et al.

(10) Patent No.: US 9,791,460 B2
(45) Date of Patent: Oct. 17, 2017

(54) BIOMARKERS USEFUL IN LIVER FIBROSIS DIAGNOSIS

(71) Applicant: Industrial Technology Research Institute, Hsin Chu (TW)

(72) Inventors: Tzu-Ling Tseng, Chiayi (TW); Hung-Yi Li, Xinying (TW); Yen-Peng Li, Taipei (TW); Angelina Huai-Lo Lee, Shalu Township (TW); Yi-Chen Liu, Miaoli (TW); Ping-Fu Cheng, Xizhou Township (TW); Wei-Ya Lin, Dali (TW); Hong-Zen Yeh, Taichung (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 14/105,891

(22) Filed: Dec. 13, 2013

(65) Prior Publication Data

US 2014/0106370 A1    Apr. 17, 2014

Related U.S. Application Data

(63) Continuation of application No. 12/628,758, filed on Dec. 1, 2009, now abandoned.

(60) Provisional application No. 61/119,077, filed on Dec. 2, 2008.

(51) Int. Cl.
| | | |
|---|---|---|
| *G01N 33/53* | (2006.01) |
| *G01N 33/49* | (2006.01) |
| *G01N 33/50* | (2006.01) |
| *G01N 33/576* | (2006.01) |
| *G01N 33/487* | (2006.01) |
| *G01N 33/68* | (2006.01) |

(52) U.S. Cl.
CPC ....... *G01N 33/6893* (2013.01); *G01N 33/487* (2013.01); *G01N 33/49* (2013.01); *G01N 33/50* (2013.01); *G01N 33/53* (2013.01); *G01N 33/576* (2013.01); *G01N 33/5067* (2013.01); *G01N 2333/70539* (2013.01); *G01N 2333/96494* (2013.01); *G01N 2333/9723* (2013.01); *G01N 2800/085* (2013.01)

(58) Field of Classification Search
CPC ..... G01N 33/6893; G01N 2333/70539; G01N 2333/96494; G01N 2333/9723; G01N 2800/085; G01N 33/53; G01N 33/49; G01N 33/50; G01N 33/576; G01N 33/487; G01N 33/5067
USPC ...... 435/7.1, 7.21, 7.23, 7.4, 7.8, 7.91, 7.94, 435/16, 23, 973, 975; 436/503, 518, 536, 436/547, 548; 530/388.2, 388.25, 388.26, 530/388.8, 388.85, 389.1, 389.3, 389.7, 530/391.1
See application file for complete search history.

(56) References Cited

U.S. PATENT DOCUMENTS

| | | | |
|---|---|---|---|
| 6,610,484 B1 * | 8/2003 | Hung | 435/6.14 |
| 6,631,330 B1 | 10/2003 | Poynard | |
| 7,141,380 B2 | 11/2006 | Volker et al. | |
| 2003/0232367 A1 | 12/2003 | Weinstein et al. | |
| 2009/0047694 A1 * | 2/2009 | Shuber | 435/15 |

OTHER PUBLICATIONS

Leroy et al., 2004. Circulating matrix metalloproteinases 1, 2, 9 and their inhibitors TIMP-1 and TIMP-2 as serum markers of liver fibrosis in patients with chronic hepatitis C: comparison with PIINP and hyaluronic acid. Am. J. Gastroenterol. 99: 271-279.*
Chung et al., 2004. Correlation between plasma levels of matrix metalloproteinase (MMP)-9/MMP-2 ration and alphafetoproteins in chronic hepatitis carrying hepatitis B virus. J. Gastroenterol. Hepatol. 19: 565-571.
El-Shorbagy et al., 2004. Non-invasive markers and predictors of severity of hepatic fibrosis in HCV patients Sharkia Governorate, Egypt. J. Egypt. Soc. Parasitol. 34: 459-478.
Gangadharan et al. "Novel Serum Biomarker Candidates for Liver Fibrosis in Hepatitis C Patients"; Clinical Chemistry 53:10 1792-1799 (2007), and supplemental online data.
Gressner et al. "Biomarkers of Liver Fibrosis: Clinical Translation of Molecular Pathogenesis or Based on Liver-Dependent Malfunction Tests"; Science Direct, Clinics Chimica Acta 381:107-113 (2007).
Malaguarnera et al., 2000. Increase of serum beta2-microglobulin in patients affected by HCV correlated hepatocellular carcinoma. Eur. J. Gastroenterol. Hepatol. 12: 937-939.
Mangoud et al., 2004. Non-histological assessment of liver fibrosis in HCV infection. J. Egypt. Soc. Parasitol. 34: 383-395.
Munteanu et al. "Noninvasive Biomarkers for the Screening of Fibrosis, Steatosis and Steatohepatitis in Patients with Metabolic Risk Factors: Fibro Test-Fibro MaxTM Experience"; Reviews; J. Gastrointestin Liver Dis; 17(2):187-191 (2008).
Okuno et al., 1997. Retinoids exacerbate rat liver fibrosis by inducing the activation of latent TGF-beta in liver stellate cells. Hepatol. 26: 913-921.
Sebastiani et al. "no Invasive Fibrosis Biomarkers Reduce but Not Substitute the Need for Liver Biopsy" World J. Gastroenterol; 12(23); 3682-3694 (2006).
Ward et al., 2006. Preclinical and post-treatment changes in the HCC-associated serum proteome. Brit. J. Cancer 95: 1379-1383.
Zhang et al., 1999. Increased expression of plasminogen activator and plasminogen activator inhibitor during liver fibrogenesis of rats: role of stellate cells. J. Hepatol. 31: 703-711.

* cited by examiner

*Primary Examiner* — Gail R Gabel
(74) *Attorney, Agent, or Firm* — Cesari and McKenna, LLP

(57) ABSTRACT

Identification of urokinase-type plasminogen, matrix metalloproteinase 9, and β-2-microglobulin as novel biomarkers associated with liver fibrosis and uses thereof in diagnosing liver fibrosis.

2 Claims, No Drawings

BIOMARKERS USEFUL IN LIVER FIBROSIS DIAGNOSIS

RELATED APPLICATIONS

This application claims priority to U.S. patent application Ser. No. 12/628,758, filed on Dec. 1, 2009, which claims priority to U.S. Provisional Application No. 61/119,077, filed on Dec. 2, 2008. The contents of the prior applications are hereby incorporated by reference in their entirety.

BACKGROUND OF THE INVENTION

Liver fibrosis involves excessive accumulation of extracellular matrix proteins (e.g., collagen) on liver cells, resulting in scar tissues. It occurs in most chronic liver diseases, such as metabolic liver diseases and those associated with hepatitis B or C infection and alcohol consumption. Advanced liver fibrosis leads to cirrhosis, liver cancer, liver failure, and portal hypertension.

Currently, liver biopsy is an optimal approach for detecting liver fibrosis and determining its severity. However, liver biopsy, an invasive procedure, is not an ideal diagnostic approach.

Non-invasive serology assays, based on fibrosis-associated serum biomarkers, have been developed for diagnosing liver fibrosis. The accuracy and sensitivity of such assays rely heavily on the biomarkers used. Thus, it is of great importance to identify reliable biomarkers that differentiate fibrosis patients from non-fibrosis humans with high sensitivity.

SUMMARY OF THE INVENTION

The present invention is based on an unexpected identification of three new serum biomarkers, i.e., urokinase-type plasminogen activator (uPA), matrix metalloproteinase 9 (MMP9; GenBank Accession Number), and beta-2-microglobulin ($\beta$-2MG), for diagnosing liver fibrosis.

Accordingly, one aspect of this invention features a method for diagnosing liver fibrosis based on the expression level of one or more of the three biomarkers listed above, and optionally in combination with one or more additional serum biomarkers, such as glutamic oxaloacetic transaminase (GOT), glutamic pyruvic transaminase (GPT), and alpha-fetoprotein (AFP).

The just-described diagnostic method includes at least four steps: (i) obtaining a blood sample from a human subject suspected of having liver fibrosis (e.g., a hepatitis B or C virus carrier, or a patient suffering from an alcohol-related liver disease or a metabolic liver disease), (ii) detecting in the blood sample the expression level of one or more of the biomarkers listed above, (iii) calculating a disease score based on the expression level, (iv) determining whether the subject has fibrosis based on the disease score. Optionally, the diagnostic method includes, after step (iv), additional step (v): assessing the subject's fibrosis stage based on the disease score as compared to pre-determined cutoff values indicating different fibrosis stage. The term "diagnosing" used herein refers to determining presence/absence of liver fibrosis in a subject (e.g., a human) or assessing the disease stage in a subject. A blood sample can be any sample obtained from blood, such as a serum sample or a plasma sample.

The disease score can be determined by subjecting the biomarker expression level to discriminant function analysis, ridge regression analysis, or logistic regression analysis.

Another aspect of this invention features a diagnostic kit containing at least two antibodies (e.g., whole immunoglobulin molecules), one being specific to uPA, MMP9, or $\beta$-2MG and the other being specific to uPA, MMP9, $\beta$-2MG, GOT, GPT, or AFP. These two antibodies have different antigen-specificities. Preferably, the kit consists essentially of the antibodies mentioned above, i.e., containing only antibodies specific to antigens to be detected (e.g., fibrosis-associated biomarkers) for diagnosing liver fibrosis. In one example, the kit contains an anti-uPA antibody, an anti-MMP9 antibody, and an anti-$\beta$-2MG antibody.

Also within the scope of this invention is use of any of antibodies mentioned above in diagnosing liver fibrosis or in manufacturing a liver fibrosis diagnostic kit.

The details of one or more embodiments of the invention are set forth in the description below. Other features or advantages of the present invention will be apparent from the following detailed description of several embodiments, and also from the appended claims.

DETAILED DESCRIPTION OF THE INVENTION

In one aspect, the present invention relates to a method for diagnosing liver fibrosis based on a subject's blood level of biomarkers uPA, MMP9, $\beta$-2MG, a combination thereof, or a combination of (a) one or more of uPA, MMP9 and $\beta$-2MG, and (b) one or more additional fibrosis biomarkers (e.g., GOT, GPT, and AFP). This method can be applied to a human patient in need to determine presence/absence of fibrosis in that patient or his or her fibrosis stage. The human patient can be a carrier of HBV or HCV, or a patient suffering from an alcohol-related disease (e.g., fatty liver and alcoholic hepatitis), a metabolic liver disease, or liver cancer.

Human uPA has two isoforms, both of which can be used in the diagnostic method of this invention. The GenBank Accession Numbers of isoform 1 is NP_002649.1 (18 Oct. 2009) and isoform 2 is NP_001138503.1 (18 Oct. 2009). The GenBank Accession numbers of the other two novel markers, MMP9 and $\beta$-2MG, are NP_004985.2 (22 Nov. 2009) and NP_004039.1 (25 Oct. 2009), respectively.

To practice the method of this invention, a blood sample can be obtained from a subject suspected of having liver fibrosis and the level of one or more of the biomarkers mentioned above can be determined by a conventional method, e.g., ELISA and Westernblot. Data indicating the level(s) of the biomarker(s) is subjected to a suitable analysis (e.g., discriminate function analysis, logistic regression analysis, ridge regression analysis, or principal component analysis) to generate a disease score (e.g., represented by a numeric number) that characterizes the blood profile of the biomarkers. When necessary, clinical factors (e.g., age and gender) can be taken into consideration. The disease score is then compared with a cutoff value that distinguishes presence or absence of liver fibrosis or with a set of cutoff values that distinguish different fibrosis stages to assess whether the subject has liver fibrosis and if so, in which disease stage. The cutoff values can be determined by analyzing the blood profile of the same biomarkers via the same analysis method in fibrosis-free subjects and in different-staged liver fibrosis patients. For example, it can be the middle point between the disease score of fibrosis-free subjects and that of fibrosis patients.

Described below is an exemplary procedure for determining the aforementioned cutoff values based on factors identified to be associated with different staged fibrosis:

(1) assigning liver fibrosis patients to different groups according to their disease conditions (e.g., fibrosis stages and risk factors);

(2) determining potential factors in the patients that possibly correlate with fibrosis stages;

(3) identifying those from the potential factors that differ significantly among the different patient groups by univariate analysis;

(4) subjecting the identified factors to discriminant function analysis, logistic regression analysis, ridge regression analysis, or generalized linear model to assess the independent value of each factor in fibrosis diagnosis;

(5) establishing a discriminant, ridge regression, or logistic regression model (e.g., a formula) to calculate a disease score based on the identified factors (including fibrosis-associated biomarkers, as well as clinical factors if applicable), and (6) determining a cutoff value for each disease stage based on a disease score (e.g., mean value) representing each patient group, as well as other relevant factors, such as sensitivity, specificity, positive predictive value (PPV) and negative predictive value (NPV).

The discriminant, ridge regression, or logistic regression model established following the above procedure can be assessed for its diagnosis value by a receiver-operating characteristic (ROC) analysis to create a ROC curve. An optimal multivariable model provides a large Area under Curve (AUC) in the ROC analysis. See the models described in Examples 1-3 below.

Also within the scope of this invention is a kit used in the above-described diagnostic method. This kit contains one or more antibodies specific to fibrosis-associated biomarkers uPA, MMP9, $\beta$-2MG, and, optionally, others of interest (e.g., GOT, GPT, and AFP). In one example, the kit includes two different antibodies (i.e., a coating antibody and a detecting antibody) that bind to the same biomarker. Typically, the detecting antibody is conjugated with a molecule which emits a detectable signal either on its own or via binding to another agent. The term "antibody" used herein refers to a whole immunoglobulin or a fragment thereof, such as Fab or $F(ab')_2$ that retains antigen-binding activity. It can be naturally occurring or genetically engineered (e.g., single-chain antibody, chimeric antibody, or humanized antibody).

The antibodies included in the kit of this invention can be obtained from commercial vendors. Alternatively, they can be prepared by conventional methods. See, for example, Harlow and Lane, (1988) Antibodies: A Laboratory Manual, Cold Spring Harbor Laboratory, New York. To produce antibodies against a particular biomarker as listed above, the marker, optionally coupled to a carrier protein (e.g., KLH), can be mixed with an adjuvant, and injected into a host animal. Antibodies produced in the animal can then be purified by affinity chromatography. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, CpG, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*. Polyclonal antibodies, i.e., heterogeneous populations of antibody molecules, are present in the sera of the immunized animal.

Monoclonal antibodies, i.e., homogeneous populations of antibody molecules, can be prepared using standard hybridoma technology (see, for example, Kohler et al. (1975) Nature 256, 495; Kohler et al. (1976) Eur. J. Immunol. 6, 511; Kohler et al. (1976) Eur J Immunol 6, 292; and Hammerling et al. (1981) Monoclonal Antibodies and T Cell Hybridomas, Elsevier, N.Y.). In particular, monoclonal antibodies can be obtained by any technique that provides for the production of antibody molecules by continuous cell lines in culture such as described in Kohler et al. (1975) Nature 256, 495 and U.S. Pat. No. 4,376,110; the human B-cell hybridoma technique (Kosbor et al. (1983) Immunol Today 4, 72; Cole et al. (1983) Proc. Natl. Acad. Sci. USA 80, 2026, and the EBV-hybridoma technique (Cole et al. (1983) Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies of the invention may be cultivated in vitro or in vivo. The ability to produce high titers of monoclonal antibodies in vivo makes it a particularly useful method of production.

Moreover, antibody fragments can be generated by known techniques. For example, such fragments include, but are not limited to, $F(ab')_2$ fragments that can be produced by pepsin digestion of an antibody molecule, and Fab fragments that can be generated by reducing the disulfide bridges of $F(ab')_2$ fragments.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

EXAMPLE 1

Diagnosing Liver Fibrosis in HCV-Positive Patients Based on Serum Levels of uPA, MMP9, $\beta$-2MG, and Other Fibrosis-Related Markers Materials and Methods
(i) Patients 140 HCV-positive patients (determined by a serology test via an immunoassay ELISA or RIA) and 93 healthy volunteers were participated in this study. Both the patients and the healthy volunteers were randomly assigned to a training set (n=148) and to a testing set (n=85). All of them were subjected to routine laboratory tests, including examination of a liver panel (GOT/AST, GPT/ALT, total serum bilirubin, alkine phosphatase, and albumin), prothrombine time/international normalized ratio (INR), AFP, tests to exclude other causes of liver disease, liver ultrasound, upper endoscopy, and modified Skinner survey (for determining alcohol consumption habit).

(ii) Biopsy Analysis

Liver biopsies were obtained from the patients and their histological features were analyzed according to the METAVR scoring system. Briefly, these samples (more than 10 mm in length) were fixed, paraffin embedded, and stained with hematoxylin eosin safran and Masson's trichrome to identify lesions or picrosirius red for collagen detection. The fibrosis stage (i.e., the amount of fibrosis) of each liver biopsy was assessed according to the following criteria:

F0: no fibrosis (healthy),
F1: portal fibrosis without septa,
F2: few septa,
F3: numerous septa without cirrhosis, and
F4: cirrhosis.

The grade (i.e., the level of inflammation caused by HCV infection) of each biopsy was also determined following a conventional method.

(iii) Serology Analysis

Ten milliliters of venous blood was drawn from each patient, collected in a tube without additives, and kept still at room temperature for 30 minutes. The blood sample was then centrifuged at 4° C., 1600 g for 15 minutes and the supernatant serum sample was collected.

The level of serum uPA was measured using the IMU-BIND uPA ELISA kit (American Diagnostica inc), following the instructions provided by the manufacturer. Briefly, serum samples were diluted 1/20 in a sample diluent included in the kit. 100 μL of an uPA standard (provided in the kit) or a diluted sample were placed in a microtest plate pre-coated with a murine anti-uPA monoclonal antibody. The plate was sealed, incubated at 4° C. overnight, and then washed 4 times with a wash buffer. A biotinylated anti-uPA antibody was then added to the plate. After being incubated at room temperature for 1 hour, the plate was washed and a streptavidin conjugated horse radish peroxidase (HRP) was added. One hour later, a solution containing a HRP substrate, i.e., perborate/3'3,5,5,-tetramethylbenzidine (TMB), was added to the plate, which was kept at room temperature for 20 minutes to allow the enzymatic reaction take place. The reaction was stopped by addition of 50 μL 0.5N $H_2SO_4$ and the absorbance at 450 nm was measured using Spectramax M5 (Molecular Devices). A standard calibration curve was constructed using a four-parameter fit (SoftMax Pro software, Molecular Devices). The serum uPA level was then determined based on the absorbance value versus the standard curve. All measurements were performed in triplicate according to the manufacturer's instructions.

The serum level of MMP9 was determined by the Quantikine MMP9 Immunoassay (R&D Systems, Minneapolis, Minn.). This assay is designed to measure the total amount of MMP-9, including both its 92 kDa precursor and 82 kDa mature forms. Briefly, a diluted serum sample (1:100) was placed in a microwell plate pre-coated with an anti-human MMP9 antibody. Two hours later, the plate was washed and a biotinylated anti-human MMP9 antibody was added. The plate was included for one hour at room temperature and a streptavidin conjugated HRP was added followed by addition of TMB. The enzymatic reaction was terminated by 1 mol/L sulphuric acid and the absorbance at 450 nm-540 nm was measured using microplate reader Spectramax M5 (Molecular Devices). The serum MMP9 level was determined as described above based on the absorbance value. All measurements were performed in triplicate according to the manufacturer's instructions.

The serum β-2MG level was determined using a sandwich enzyme immunoassay kit (GenWay Biotech) as follows. 20 μL of a diluted serum sample (1:100) were placed in a microplate pre-coated with a mouse monoclonal anti-β-2MG antibody and mixed with 200 μL of a sample diluent. The mixture was incubated for 30 minutes at 37° C. The plate was washed 4 times with distilled water and a HRP-conjugated sheep anti-β-2MG antibody was then added. After being incubated for 30 minutes at 37° C., the plate was washed again followed by addition of TMB. 20 minutes later, the enzymatic reaction was terminated by 1N HCl. The absorbance at 450 nm was measured with Spectramax M5 (Molecular Devices) and the β-2MG level was determined following the method described above. All measurements were performed in triplicate according to the manufacturer's instructions.

The serum levels of other fibrosis-related markers, such as GOT, GPT, or AFP were determined by conventional methods.

(iv) Determining Disease Scores

The correlations between the expression level of uPA, MMP9, β-2MG, or a combination thereof and fibrosis stages were determined via discriminant analysis, ridge regression analysis, or logistic regression analysis, taking into consideration clinical factors when applicable. The diagnostic value for each of the three biomarkers or a combination thereof was assessed based on sensitivity, specificity, positive predictive values, and negative predictive values. The sensitivity, specificity, positive and negative predictive values were determined by a screen test, in which the points on the ROC curve that correspond to different cutoff values represent test positive. All statistical analysis was conducted with the R software.

Results (i) Patient Characteristics

The patient characteristics, including clinical factors obtained from the laboratory tests mentioned above and serum levels of fibrosis-related biomarkers, were shown in Table 1 below:

TABLE 1

Patient Characteristics

|  | Training set (n = 148) | Testing set (n = 85) | P-value (univariate analysis) |
|---|---|---|---|
| Age, mean (SD) | 45.87 (14.53) | 50.26 (13.61) | 0.02 |
| Female, n (%) | 84 (57%) | 43 (51%) | 0.44 |
| Fibrosis Stage, n (%) | | | |
| No fibrosis (Healthy, F0) | 63 (43%) | 30 (35%) | 0.34 |
| Fibrosis (F1 + F2 + F3) | 55 (37%) | 35 (41%) | 0.64 |
| Cirrhosis (F4) | 30 (20%) | 20 (24%) | 0.67 |
| Serum Biochemical Makers, mean (SD) | | | |
| GOT/AST, IU/L | 45.28 (51.78) | 57.63 (55.94) | 0.11 |
| GPT/ALT, IU/L | 57.73 (81.9) | 72.95 (87.08) | 0.19 |
| T. Bilirubin, μmol/L | 15.94 (20.55) | 23.76 (19.46) | 0.03 |
| Albumin, g/L | 44.6 (5.6) | 40.04 (6.2) | 0.001 |
| AFP, ng/ml | 8.85 (17.09) | 19.96 (53.74) | 0.11 |
| Novel Serum Markers, mean (SD) | | | |
| uPA, ng/ml | 0.82 (0.59) | 0.96 (0.78) | 0.13 |
| MMP9, μg/ml | 0.22 (0.2) | 0.22 (0.2) | 0.88 |
| β-2MG, μg/ml | 2.17 (3.14) | 1.82 (0.95) | 0.20 |

(ii) Association of Serum uPA, MMP9, or β-2MG and Other Clinical Factors with Liver Fibrosis As shown in Table 2 below, the serum level of uPA, MMP9, or β-2MG correlates with fibrosis presence/absence and severity in both training and testing patient sets.

TABLE 2

Association of Age, Gender, and Serum Biochemical Markers with Liver Fibrosis

|  | Training set (n = 148) | | | Testing set (n = 85) | | |
|---|---|---|---|---|---|---|
|  | Healthy~F1 (n = 73) | F2~F4 (n = 75) | P-value (univariate analysis) | Healthy~F1 (n = 40) | F2~F4 (n = 45) | P-value (univariate analysis) |
| Age, mean(SD) | 37.59 (11.31) | 53.93 (12.7) | 7.65E−14 | 44.1 (9.36) | 55.73 (14.52) | 3.03E−05 |
| Female, n (%) | 46 (63%) | 38 (51%) | 0.18 | 17 (43%) | 26 (58%) | 0.23 |
| GOT/AST, IU/L | 21.37 (23.2) | 72.98 (61.33) | 1.677E−08 | 28.8 (22.4) | 90.57 (64.35) | 3.03E−06 |
| GPT/ALT, IU/L | 25.96 (48.2) | 89.94 (95.7) | 1.701E−06 | 32.38 (44.2) | 109.84 (99.7) | 1.07E−05 |
| T. Bilirubin,, μmol/L | 11.18 (4.21) | 21.54 (29.11) | 0.1 | 15.18 (13.1) | 26.12 (20.42) | 0.09 |
| Albumin, g/L | 46.87 (2.6) | 36.18 (5.73) | 6.505E−07 | 45 (4.73) | 38.55 (5.88) | 0.020 |
| AFP, ng/ml | 2.98 (2.06) | 16.92 (24.1) | 0.0001 | 3.84 (2.78) | 40.86 (77.21) | 0.019 |
| Novel Serum Markers, mean(SD) | | | | | | |
| uPA, ng/ml | 0.48 (0.24) | 1.14 (0.64) | 3.988E−13 | 0.49 (0.21) | 1.39 (0.85) | 8.25E−09 |
| MMP9, μg/ml | 0.3 (0.2) | 0.14 (0.16) | 2.653E−07 | 0.33 (0.24) | 0.11 (0.07) | 9.77E−07 |
| β-2MG, μg/ml | 1.34 (0.51) | 2.98 (4.25) | 0.0013 | 1.22 (0.38) | 2.35 (0.99) | 1.99E−09 |

Low serum levels of uPA and β-2MG were observed in patients with no or little fibrosis while these levels elevated significantly in patients having mild or severe fibrosis. More specifically, in the training set, the mean serum levels of uPA in F0, F1, F2, F3, and F4 were found to be 0.46 ng/ml, 0.61 ng/ml, 0.75 ng/ml, 0.86 ng/ml, and 1.66 ng/ml, respectively, and the mean serum levels of β-2MG in F0, F1, F2, F3, and F4 were found to be 1.26 μg/ml, 1.86 μg/ml, 2.22 μg/ml, 2.38 μg/ml, and 4 μg/ml, respectively. On the other hand, healthy patients or patients with little fibrosis showed a significantly higher serum level of MMP9 than patients with mild or severe fibrosis. The mean serum levels of this marker were found to be 0.33 μg/ml, 0.16 μg/ml, 0.19 μg/ml, 0.14 μg/ml, and 0.1 μg/ml, respectively. Very similar data was obtained from the testing set. These results indicate that uPA, MMP9, and β-2MG, individually, are reliable markers for diagnosing liver fibrosis.

(iii) Two-Marker Models for Diagnosing Liver Fibrosis

The results from this study indicate that the combined levels of any two of uPA, MMP9, β-2MG, GOT, GPT, AFP and clinical factors can be used as reliable markers for diagnosing liver fibrosis. Shown below are two exemplary two marker-models, i.e., uPA+MMP 9, and uPA+GPT, including equations for calculating disease scores based on the combined levels of each two-marker pairs. These equations were established by discriminant function analysis, logistic regression analysis, or ridge regression analysis. Also shown below are tables (i.e., Tables 3-8) listing cutoff values, sensitivities, specificities, negative predictive values (NPV) and positive predictive values (PPV), and area under the ROC curve (AUROC) for these two-marker models.

uPA and MMP9

Discriminant Function Analysis:

Disease Score=1.4829×uPA (ng/ml)−3.2605×MMP9 (μg/ml)+5

TABLE 3

Cutoff Values Representing Different Fibrosis Stage in a uPA + MMP9 Discriminant Model

|  | Training set (n = 148) | | | | Testing set(n = 85) | | | |
|---|---|---|---|---|---|---|---|---|
| Fibrosis Stage | F1~F4 | F2~F4 | F3~F4 | F4 | F1~F4 | F2~F4 | F3~F4 | F4 |
| Number of patients (%) | 85 (57%) | 75 (51%) | 52 (35%) | 30 (20%) | 55 (65%) | 45 (53%) | 36 (42%) | 20 (24%) |
|  | Healthy vs. F1~F4 | Healthy, F1 vs. F2~F4 | Healthy, F1~F2 vs. F3~F4 | Healthy, F1~F3 vs. F4 | Healthy vs. F1~F4 | Healthy, F1 vs. F2~F4 | Healthy, F1~F2 vs. F3~F4 | Healthy, F1~F3 vs. F4 |
| Cutoff Value | 5.4310 | 5.6243 | 5.8955 | 6.0554 | 5.4310 | 5.6243 | 5.8955 | 6.0554 |
| Sensitivity (%) | 74 | 72 | 71 | 80 | 78 | 80 | 75 | 85 |
| Specificity (%) | 90 | 90 | 90 | 90 | 97 | 95 | 90 | 80 |
| NPV (%) | 72 | 76 | 85 | 95 | 71 | 81 | 83 | 95 |
| PPV (%) | 91 | 89 | 79 | 67 | 98 | 95 | 84 | 57 |
| AUROC | 0.9 | 0.89 | 0.89 | 0.93 | 0.98 | 0.96 | 0.93 | 0.91 |

The coefficient value of uPA was 0.741 to 1.763, preferably 1.26 to 1.705, and that of MMP9 was −7.553 to −2.839, preferably −3.75 to −2.771.

Logistic Regression Analysis:

Disease Score=exp (Logit_value)/(1+exp (Logit_value)), in which

Logit_value=−2.2416+3.2059×uPA (ng/ml)−5.6316×MMP9 (μg/ml)

TABLE 4

Cutoff Values Representing Different Fibrosis Stage in a uPA + MMP9 Logistic Regression Model

|  | Training set (n = 148) | | | | Testing set (n = 85) | | | |
|---|---|---|---|---|---|---|---|---|
| Fibrosis Stage | F1~F4 | F2~F4 | F3~F4 | F4 | F1~F4 | F2~F4 | F3~F4 | F4 |
| Number of patients (%) | 85 (57%) | 75 (51%) | 52 (35%) | 30 (20%) | 55 (65%) | 45 (53%) | 36 (42%) | 20 (24%) |
|  | Healthy vs. F1~F4 | Healthy, F1 vs. F2~F4 | Healthy, F1~F2 vs. F3~F4 | Healthy, F1~F3 vs. F4 | Healthy vs. F1~F4 | Healthy, F1 vs. F2~F4 | Healthy, F1~F2 vs. F3~F4 | Healthy, F1~F3 vs. F4 |
| Cutoff Value | 0.2704 | 0.3347 | 0.4548 | 0.5594 | 0.2704 | 0.3347 | 0.4548 | 0.5594 |
| Sensitivity (%) | 73 | 72 | 73 | 80 | 78 | 80 | 75 | 85 |
| Specificity (%) | 90 | 90 | 90 | 90 | 97 | 95 | 90 | 80 |
| NPV (%) | 71 | 76 | 86 | 95 | 71 | 81 | 83 | 95 |
| PPV (%) | 91 | 89 | 79 | 67 | 98 | 95 | 84 | 57 |
| AUROC | 0.9 | 0.89 | 0.89 | 0.93 | 0.97 | 0.96 | 0.94 | 0.91 |

The coefficient of intercept was −3 to −1.48, preferably −2.578 to −1.905, the coefficient of uPA was 2.49 to 3.91, preferably 2.725 to 3.687, and the coefficient of MMP9 was −8.01 to −3.24, preferably −6.477 to −4.787.

Ridge Regression Analysis:

Disease Score=1.6641+1.7227×uPA (ng/ml)−1.9821×MMP9 (μg/ml)

TABLE 5

Cutoff Values Representing Different Fibrosis Stage in a uPA + MMP9 Ridge Regression Model

|  | Training set (n = 148) | | | | Testing set (n = 85) | | | |
|---|---|---|---|---|---|---|---|---|
| Fibrosis Stage | F1~F4 | F2~F4 | F3~F4 | F4 | F1~F4 | F2~F4 | F3~F4 | F4 |
| Number of patients | 85 (57%) | 75 (51%) | 52 (35%) | 30 (20%) | 55 (65%) | 45 (53%) | 36 (42%) | 20 (24%) |
|  | Healthy vs. F1~F4 | Healthy, F1 vs. F2~F4 | Healthy, F1~F2 vs. F3~F4 | Healthy, F1~F3 vs. F4 | Healthy vs. F1~F4 | Healthy, F1 vs. F2~F4 | Healthy, F1~F2 vs. F3~F4 | Healthy, F1~F3 vs. F4 |
| Cutoff Value | 2.5222 | 2.6029 | 2.9505 | 3.1213 | 2.5222 | 2.6029 | 2.9505 | 3.1213 |
| Sensitivity (%) | 72 | 75 | 67 | 80 | 73 | 84 | 72 | 85 |
| Specificity (%) | 90 | 90 | 90 | 90 | 97 | 95 | 92 | 85 |
| NPV (%) | 70 | 78 | 83 | 95 | 66 | 84 | 82 | 95 |
| PPV (%) | 91 | 89 | 78 | 67 | 98 | 95 | 87 | 63 |
| AUROC | 0.89 | 0.89 | 0.89 | 0.93 | 0.97 | 0.96 | 0.95 | 0.92 |

The coefficient of intercept was 1.430 to 2.531, preferably 1.414 to 1.914, that of uPA was 1.191 to 1.938, preferably 1.464 to 1.895, and that of MMP9 was −4.428 to −1.501, preferably −2.279 to −1.685.

uPA and GPT

Discriminant Function Analysis:

Disease Score=1.5351×uPA (ng/ml)+0.0083×GPT (IU/L)+5

TABLE 6

Cutoff Values Representing Different Fibrosis Stage in a uPA + GPT Discriminant Model

|  | Training set(n = 145) | | | | Testing set(n = 84) | | | |
|---|---|---|---|---|---|---|---|---|
| Fibrosis Stage | F1~F4 | F2~F4 | F3~F4 | F4 | F1~F4 | F2~F4 | F3~F4 | F4 |
| Number of patients (%) | 82 (57%) | 72 (50%) | 50 (34%) | 30 (21%) | 54 (64%) | 44 (52%) | 36 (43%) | 20 (24%) |

TABLE 6-continued

Cutoff Values Representing Different Fibrosis Stage in a uPA + GPT Discriminant Model

| Fibrosis Stage | Training set(n = 145) | | | | Testing set(n = 84) | | | |
| --- | --- | --- | --- | --- | --- | --- | --- | --- |
| | F1~F4 | F2~F4 | F3~F4 | F4 | F1~F4 | F2~F4 | F3~F4 | F4 |
| | Healthy vs. F1~F4 | Healthy, F1 vs. F2~F4 | Healthy, F1~F2 vs. F3, F4 | Healthy, F1~F3 vs. F4 | Healthy vs. F1~F4 | Healthy, F1 vs. F2~F4 | Healthy, F1~F2 vs. F3, F4 | Healthy, F1~F3 vs. F4 |
| Cutoff Value | 6.3072 | 6.5753 | 7.1162 | 7.5766 | 6.3072 | 6.5753 | 7.1162 | 7.5766 |
| Sensitivity (%) | 79 | 71 | 62 | 73 | 80 | 89 | 78 | 80 |
| Specificity (%) | 90 | 90 | 89 | 90 | 90 | 90 | 85 | 84 |
| NPV (%) | 77 | 76 | 82 | 93 | 71 | 88 | 84 | 93 |
| PPV (%) | 92 | 88 | 76 | 65 | 93 | 91 | 80 | 62 |
| AUROC | 0.92 | 0.9 | 0.88 | 0.89 | 0.94 | 0.94 | 0.91 | 0.88 |

The coefficient of uPA was 0.949 to 1.750, preferably 1.305 to 1.719, and that of GPT was 0.006 to 0.017, preferably 0.007 to 0.01.

Logistic Regression Analysis:

Disease Score=exp (Logit_value)/(1+exp (Logit_value)), in which

Logit_value=−3.7206+3.8376×uPA (ng/ml)+(−0.0001)×GPT (IU/L)

TABLE 7

Cutoff Values Representing Different Fibrosis Stage in a uPA + GPT Logistic Regression Model

| Fibrosis Stage | Training set(n = 145) | | | | Testing set(n = 84) | | | |
| --- | --- | --- | --- | --- | --- | --- | --- | --- |
| | F1~F4 | F2~F4 | F3~F4 | F4 | F1~F4 | F2~F4 | F3~F4 | F4 |
| Number of patients (%) | 82 (57%) | 72 (50%) | 50 (34%) | 30 (21%) | 54 (64%) | 44 (52%) | 36 (43%) | 20 (24%) |
| | Healthy vs. F1~F4 | Healthy, F1 vs. F2~F4 | Healthy, F1~F2 vs. F3, F4 | Healthy, F1~F3 vs. F4 | Healthy vs. F1~F4 | Healthy, F1 vs. F2~F4 | Healthy, F1~F2 vs. F3, F4 | Healthy, F1~F3 vs. F4 |
| Cutoff Value | 0.3333 | 0.4303 | 0.4316 | 0.5143 | 0.3333 | 0.4303 | 0.4316 | 0.5143 |
| Sensitivity (%) | 57 | 50 | 62 | 80 | 67 | 59 | 69 | 85 |
| Specificity (%) | 90 | 90 | 89 | 90 | 93 | 95 | 94 | 88 |
| Negative predictive value (%) | 62 | 65 | 82 | 94 | 61 | 68 | 80 | 95 |
| Positive predictive value (%) | 89 | 84 | 76 | 67 | 94 | 93 | 89 | 68 |
| Area under the ROC curve | 0.85 | 0.86 | 0.88 | 0.91 | 0.87 | 0.92 | 0.94 | 0.93 |

The coefficient of intercept was −4.30 to −3.14, preferably −4.279 to −3.274, that of uPA was 3.11 to 4.57, preferably 3.262 to 4.413, and that of GPT was −0.01 to 0.002, preferably −0.00012 to −0.00008.

Ridge Regression Analysis:

Disease Score=0.9199+1.8321×uPA (ng/ml)+0.0034×GPT (IU/L)

TABLE 8

Cutoff Values Representing Different Fibrosis Stage in a uPA + GPT Ridge Regression Model

| Fibrosis Stage | Training set(n = 145) | | | | Testing set(n = 84) | | | |
| --- | --- | --- | --- | --- | --- | --- | --- | --- |
| | F1~F4 | F2~F4 | F3~F4 | F4 | F1~F4 | F2~F4 | F3~F4 | F4 |
| Number of patients (%) | 82 (57%) | 72 (50%) | 50 (34%) | 30 (21%) | 54 (64%) | 44 (52%) | 36 (43%) | 20 (24%) |

TABLE 8-continued

Cutoff Values Representing Different Fibrosis Stage in a uPA + GPT Ridge Regression Model

| Fibrosis Stage | Training set(n = 145) | | | | Testing set(n = 84) | | | |
|---|---|---|---|---|---|---|---|---|
| | F1~F4 | F2~F4 | F3~F4 | F4 | F1~F4 | F2~F4 | F3~F4 | F4 |
| | Healthy vs. F1~F4 | Healthy, F1 vs. F2~F4 | Healthy, F1~F2 vs. F3, F4 | Healthy, F1~F3 vs. F4 | Healthy vs. F1~F4 | Healthy, F1 vs. F2~F4 | Healthy, F1~F2 vs. F3, F4 | Healthy, F1~F3 vs. F4 |
| Cutoff Value | 2.3701 | 2.6192 | 2.9050 | 3.0855 | 2.3701 | 2.6192 | 2.9050 | 3.0855 |
| Sensitivity (%) | 72 | 64 | 62 | 77 | 74 | 82 | 78 | 80 |
| Specificity (%) | 90 | 90 | 89 | 90 | 93 | 95 | 94 | 83 |
| Negative predictive value (%) | 71 | 72 | 82 | 94 | 67 | 83 | 85 | 93 |
| Positive predictive value (%) | 91 | 87 | 76 | 66 | 95 | 95 | 90 | 59 |
| Area under the ROC curve | 0.89 | 0.89 | 0.88 | 0.9 | 0.93 | 0.94 | 0.94 | 0.92 |

The coefficient of intercept was 0.705 to 1.281, preferably 0.782 to 1.03, that of uPA was 1.303 to 2.052, preferably 1.557 to 2.107, and that of GPT was 0.002 to 0.009, preferably 0.0029 to 0.0039.

(iv) Three-Marker Models for Diagnosing Liver Fibrosis

Described below are exemplary three-marker models, based on the combined serum levels of three markers selected from uPA, MMP9, β-2MG, GOT, GPT, and AFP for liver fibrosis diagnosis. When necessary, clinical factors were also taken into consideration. These models were established by discriminate function analysis, logistic regression function analysis, and ridge regression function analysis. The disease scores calculated following these three-marker models were analyzed in view of fibrosis severity. Linear correlations were found between METAVIR fibrosis stages versus disease scores.

Four cutoff values indicating (i) any fibrosis (Healthy versus F1-F4); (ii) moderate fibrosis (Healthy~F1 versus F2-F4); (iii) severe fibrosis (Healthy~F2 versus F3-F4); and (iv) cirrhosis (Healthy~F3 versus F4) were determined in the training set and validated in the testing set.

uPA, MMP9, and β-2MG

Discriminant Function Analysis:

Disease Score=1.4159×uPA (ng/ml)−3.0399×MMP9 (μg/ml)+0.0897×β-2MG (μg/ml)+5

TABLE 9

Cutoff Values Representing Different Fibrosis Stage in a uPA + MMP9 + β-2MG Discriminant Model

| Fibrosis Stage | Training set (n = 148) | | | | Testing set (n = 85) | | | |
|---|---|---|---|---|---|---|---|---|
| | F1~F4 | F2~F4 | F3~F4 | F4 | F1~F4 | F2~F4 | F3~F4 | F4 |
| Number of patients (%) | 85 (57%) | 75 (51%) | 52 (35%) | 30 (20%) | 55 (65%) | 45 (53%) | 36 (42%) | 20 (24%) |
| | Healthy vs. F1~F4 | Healthy, F1 vs. F2~F4 | Healthy, F1~F2 vs. F3~F4 | Healthy, F1~F3 vs. F4 | Healthy vs. F1~F4 | Healthy, F1 vs. F2~F4 | Healthy, F1~F2 vs. F3~F4 | Healthy, F1~F3 vs. F4 |
| Cutoff Value | 5.5918 | 5.7362 | 6.0726 | 6.2124 | 5.5918 | 5.7362 | 6.0726 | 6.2124 |
| Sensitivity (%) | 74 | 73 | 71 | 83 | 78 | 82 | 75 | 85 |
| Specificity (%) | 90 | 90 | 90 | 90 | 97 | 95 | 92 | 85 |
| NPV (%) | 72 | 77 | 85 | 95 | 71 | 83 | 83 | 95 |
| PPV (%) | 91 | 89 | 79 | 68 | 98 | 95 | 87 | 63 |
| AUROC | 0.91 | 0.9 | 0.9 | 0.94 | 0.98 | 0.96 | 0.94 | 0.92 |

The coefficient of uPA was 0.389 to 1.604, preferably 1.204 to 1.586, that of MMP9 was −7.321 to −2.302, preferably −3.496 to −2.584, and that of β-2MG was 0.048 to 1.114, preferably 0.076 to 0.103.

Logistic Regression Analysis:

Disease Score=exp (Logit_value)/(1+exp (Logit_value)), in which,

Logit_value=−3.8614+2.8761×uPA (ng/ml)−4.0100×MMP9(μg/ml)+0.7853×β-2MG (μg/ml)

TABLE 10

Cutoff Values Representing Different Fibrosis Stage in a uPA + MMP9 + β-2MG Logistic Regression Model

| | Training set (n = 148) | | | | Testing set (n = 85) | | | |
|---|---|---|---|---|---|---|---|---|
| Fibrosis Stage | F1~F4 | F2~F4 | F3~F4 | F4 | F1~F4 | F2~F4 | F3~F4 | F4 |
| Number of patients (%) | 85 (57%) | 75 (51%) | 52 (35%) | 30 (20%) | 55 (65%) | 45 (53%) | 36 (42%) | 20 (24%) |
| | Healthy vs. F1~F4 | Healthy, F1 vs. F2~F4 | Healthy, F1~F2 vs. F3~F4 | Healthy, F1~F3 vs. F4 | Healthy vs. F1~F4 | Healthy, F1 vs. F2~F4 | Healthy, F1~F2 vs. F3~F4 | Healthy, F1~F3 vs. F4 |
| Cutoff Value | 0.1962 | 0.2806 | 0.4863 | 0.5961 | 0.1962 | 0.2806 | 0.4863 | 0.5961 |
| Sensitivity (%) | 84 | 79 | 69 | 83 | 80 | 82 | 67 | 85 |
| Specificity (%) | 90 | 90 | 90 | 90 | 100 | 95 | 94 | 91 |
| NPV (%) | 80 | 80 | 84 | 95 | 73 | 83 | 79 | 95 |
| PPV (%) | 92 | 89 | 78 | 68 | 100 | 95 | 89 | 74 |
| AUROC | 0.94 | 0.93 | 0.91 | 0.93 | 0.99 | 0.97 | 0.95 | 0.95 |

The coefficient value of intercept was −4.9 to −2.28 and those of uPA, MMP9, and β-2MG were 2.15 to 3.6, −6.4 to −1.61, and 0.47 to 1.1, respectively. Preferably, the coefficient value of intercept, uPA, MMP9, and β-2MG were −4.441 to −3.282, 2.454 to 3.308, −4.611 to −3.409, and 0.668 to 0.903, respectively.

Ridge Regression Analysis:

Disease Score=1.4645+1.6683×uPA (ng/ml)−1.7868×MMP9 (μg/ml)+0.0926×β-2MG (μg/ml)

TABLE 11

Cutoff Values Representing Different Fibrosis Stage in a uPA + MMP9 + β-2MG Ridge Regression Model

| | Training set (n = 148) | | | | Testing set (n = 85) | | | |
|---|---|---|---|---|---|---|---|---|
| Fibrosis Stage | F1~F4 | F2~F4 | F3~F4 | F4 | F1~F4 | F2~F4 | F3~F4 | F4 |
| Number of patients (%) | 85 (57%) | 75 (51%) | 52 (35%) | 30 (20%) | 55 (65%) | 45 (53%) | 36 (42%) | 20 (24%) |
| | Healthy vs. F1~F4 | Healthy, F1 vs. F2~F4 | Healthy, F1~F2 vs. F3~F4 | Healthy, F1~F3 vs. F4 | Healthy vs. F1~F4 | Healthy, F1 vs. F2~F4 | Healthy, F1~F2 vs. F3~F4 | Healthy, F1~F3 vs. F4 |
| Cutoff Value | 2.4483 | 2.5196 | 2.9199 | 3.0791 | 2.4483 | 2.5196 | 2.9199 | 3.0791 |
| Sensitivity (%) | 75 | 77 | 69 | 83 | 75 | 87 | 72 | 85 |
| Specificity (%) | 90 | 90 | 90 | 90 | 97 | 95 | 92 | 86 |
| NPV (%) | 73 | 80 | 84 | 95 | 67 | 86 | 82 | 95 |
| PPV (%) | 91 | 89 | 78 | 68 | 98 | 95 | 87 | 65 |
| AUROC | 0.91 | 0.9 | 0.9 | 0.93 | 0.97 | 0.96 | 0.95 | 0.92 |

The coefficient of intercept was 0.558 to 2.418 (e.g., 1.245 to 1.684); those of uPA, MMP9, and β-2MG were 0.818 to 1.907 (e.g., 1.418 to 1.835), −4.677 to −0.997 (e.g., −2.055 to −1.519), and 0.076 to 0.825 (e.g., 0.079 to 0.106), respectively.

Table 12 below shows the results obtained from the testing set, following the three-marker models described above:

TABLE 12

Cutoff value Representing Different Fibrosis Stages Determined Based on Combined Serum Levels of uPA, MMP9, and β-2MG in Testing Set.

| | AUC | Cut-Off | Sensitivity | Specificity | PPV | NPV |
|---|---|---|---|---|---|---|
| Discriminant Model | | | | | | |
| Healthy vs. F1~F4 | 0.98 | 5.21 | 0.98 | 0.83 | 0.92 | 0.96 |
| | | 5.25 | 0.96 | 0.93 | 0.96 | 0.93 |
| Healthy, F1 vs. F2~F4 | 0.96 | 5.54 | 0.93 | 0.90 | 0.91 | 0.92 |
| | | 5.63 | 0.87 | 0.90 | 0.91 | 0.86 |
| Healthy, F1~F2 vs. F3~F4 | 0.94 | 6.01 | 0.81 | 0.90 | 0.85 | 0.86 |
| | | 6.10 | 0.75 | 0.92 | 0.87 | 0.83 |
| Healthy, F1~F3 vs. F4 | 0.92 | 6.62 | 0.85 | 0.91 | 0.74 | 0.95 |
| | | 6.78 | 0.70 | 0.92 | 0.74 | 0.91 |
| Logistic Regression Model | | | | | | |
| Healthy vs. F1~F4 | 0.99 | 0.09 | 0.98 | 0.90 | 0.95 | 0.96 |
| | | 0.11 | 0.93 | 0.93 | 0.96 | 0.88 |
| Healthy, F1 vs. F2~F4 | 0.97 | 0.28 | 0.82 | 0.95 | 0.95 | 0.83 |
| | | 0.35 | 0.80 | 0.95 | 0.95 | 0.81 |
| Healthy, F1~F2 vs. F3~F4 | 0.95 | 0.50 | 0.69 | 0.94 | 0.89 | 0.81 |
| | | 0.54 | 0.67 | 0.94 | 0.89 | 0.79 |
| Healthy, F1~F3 vs. F4 | 0.95 | 0.75 | 0.85 | 0.94 | 0.81 | 0.95 |
| | | 0.85 | 0.75 | 0.97 | 0.88 | 0.93 |
| Ridge Regression Model | | | | | | |
| Healthy vs. F1~F4 | 0.97 | 2.0 | 0.96 | 0.70 | 0.85 | 0.91 |
| | | 2.05 | 0.95 | 0.83 | 0.91 | 0.89 |
| Healthy, | 0.96 | 2.4 | 0.91 | 0.93 | 0.93 | 0.90 |
| F1 vs. F2~F4 | | 2.5 | 0.87 | 0.93 | 0.93 | 0.86 |
| Healthy, | 0.95 | 2.9 | 0.75 | 0.92 | 0.87 | 0.83 |
| F1~F2 vs. F3~F4 | | 3.0 | 0.72 | 0.96 | 0.93 | 0.82 |
| Healthy, | 0.92 | 3.8 | 0.75 | 0.92 | 0.75 | 0.92 |
| F1~F3 vs. F4 | | 3.9 | 0.70 | 0.95 | 0.82 | 0.91 |

Based on the results shown above, suggested cutoff value ranges for different disease stages were determined (see Table 13 below), taking into consideration sensitivity, specificity, PPV, and NPV of the training set.

TABLE 13

Suggested Cutoff Values for Different Liver Fibrosis Stage

| Fibrosis stage | Disease Score (Discriminant Model) | Disease Score (Logistic Regression Model) | Disease Score (Ridge Regression Model) |
|---|---|---|---|
| Healthy | 0~5.21 | 0~0.09 | 0~2.00 |
| Healthy~F1 | 5.21~5.26 | 0.09~0.11 | 2.00~2.05 |
| F1 | 5.26~5.55 | 0.11~0.28 | 2.05~2.40 |
| F1~F2 | 5.55~5.63 | 0.28~0.35 | 2.40~2.50 |
| F2 | 5.63~6.01 | 0.35~0.50 | 2.50~2.90 |
| F2~F3 | 6.01~6.10 | 0.50~0.54 | 2.90~3.00 |
| F3 | 6.10~6.62 | 0.54~0.75 | 3.00~3.80 |
| F3~F4 | 6.62~6.78 | 0.75~0.85 | 3.80~3.90 |
| F4 | 6.78~ | 0.85~1.00 | 3.90~ | uPA, MMP9, and GPT
Discriminant Function Analysis:
Disease Score=1.2295×uPA (ng/ml)+(−2.6571)×MMP9 (μg/ml)+0.0072×GPT (IU/L)+5

TABLE 14

Cutoff Values Representing Different Fibrosis Stage in a 3-Marker Discriminant Model

| | Training set(n = 145) | | | | Testing set(n = 84) | | | |
|---|---|---|---|---|---|---|---|---|
| Fibrosis Stage | F1~F4 | F2~F4 | F3~F4 | F4 | F1~F4 | F2~F4 | F3~F4 | F4 |
| Number of patients (%) | 82 (57%) | 72 (50%) | 50 (34%) | 30 (21%) | 54 (64%) | 44 (52%) | 36 (43%) | 20 (24%) |
| | Healthy vs. F1~F4 | Healthy, F1 vs. F2~F4 | Healthy, F1~F2 vs. F3, F4 | Healthy, F1~F3 vs. F4 | Healthy vs. F1~F4 | Healthy, F1 vs. F2~F4 | Healthy, F1~F2 vs. F3, F4 | Healthy, F1~F3 vs. F4 |
| Cutoff Value | 5.4766 | 5.6061 | 6.5738 | 6.6547 | 5.4766 | 5.6061 | 6.5738 | 6.6547 |
| Sensitivity (%) | 85 | 85 | 56 | 77 | 93 | 91 | 72 | 75 |
| Specificity (%) | 90 | 90 | 89 | 90 | 97 | 83 | 85 | 77 |
| Negative predictive value (%) | 83 | 86 | 79 | 94 | 88 | 89 | 80 | 90 |
| Positive predictive value (%) | 92 | 90 | 74 | 66 | 98 | 85 | 78 | 50 |
| Area under the ROC curve | 0.95 | 0.92 | 0.89 | 0.91 | 0.99 | 0.96 | 0.91 | 0.86 |

The coefficient values of uPA, MMP9, and GPT were 0.539 to 1.456 (e.g., 1.045 to 1.414), −6.988 to −2.053 (e.g., −3.056 to −2.391), and 0.004 to 0.014 (e.g., 0.006 to 0.008), respectively.

Logistic Regression Analysis:

Disease Score=exp (Logit-value)/(1+exp (Logit-value)), in which

Logit-value=−2.1715+3.3171×uPA (ng/ml)+(−6.2008)×MMP9 (μg/ml)+(−0.0018)×GPT (IU/L)

The coefficient value of intercept was 1.154 to 2.300 (e.g., 1.277 to 1.727) and those of uPA, MMP9, and GPT were 1.075 to 1.941 (e.g., 1.401 to 1.895), −4.192 to −1.218 (e.g., −2.057 to −1.52), and 0.001 to 0.007 (e.g., 0.0024 to 0.0032), respectively.

(v) Four-Marker Models for Diagnosing Liver Fibrosis

The results obtained from this study indicate that combinations of any four factors of uPA, MMP9, β-2MG, GOT, GPT, AFP, taking into account clinical factors when applicable, are reliable markers for diagnosing liver fibrosis. Described below is an exemplary 4-marker model composed of uPA, MMP9, β-2MG, and GPT. The results are shown in Tables 17-19.

TABLE 15

Cutoff Values Representing Different Fibrosis Stage in a 3-Marker Logistic Regression Model

| | Training set(n = 145) | | | | Testing set(n = 84) | | | |
|---|---|---|---|---|---|---|---|---|
| Fibrosis Stage | F1~F4 | F2~F4 | F3~F4 | F4 | F1~F4 | F2~F4 | F3~F4 | F4 |
| Number of patients (%) | 82 (57%) | 72 (50%) | 50 (34%) | 30 (21%) | 54 (64%) | 44 (52%) | 36 (43%) | 20 (24%) |
| | Healthy vs. F1~F4 | Healthy, F1 vs. F2~F4 | Healthy, F1~2 vs. F3, F4 | Healthy, F1~3 vs. F4 | Healthy vs. F1~F4 | Healthy, F1 vs. F2~F4 | Healthy, F1~2 vs. F3, F4 | Healthy, F1~3 vs. F4 |
| Cutoff Value | 0.2803 | 0.3435 | 0.4456 | 0.5320 | 0.2803 | 0.3435 | 0.4456 | 0.5320 |
| Sensitivity (%) | 70 | 71 | 76 | 80 | 70 | 75 | 75 | 85 |
| Specificity (%) | 90 | 90 | 89 | 90 | 96 | 95 | 90 | 81 |
| Negative predictive value (%) | 70 | 76 | 88 | 94 | 64 | 78 | 83 | 95 |
| Positive predictive value (%) | 90 | 88 | 79 | 67 | 97 | 94 | 84 | 58 |
| Area under the ROC curve | 0.88 | 0.88 | 0.9 | 0.93 | 0.96 | 0.95 | 0.93 | 0.91 |

The coefficient value of intercept was −2.95 to −1.38 (e.g., −2.497 to −1.846) and those of uPA, MMP9, and GPT were 2.56 to 4.07 (e.g., 2.82 to 3.649), −8.73 to −3.66 (e.g., −7.131 to −5.271), and −0.02 to 0.001 (e.g., −0.0021 to −0.0015), respectively.

Ridge Regression Analysis:

Disease Score=1.5020+1.6479×uPA (ng/ml)−1.7885×MMP9 (μg/ml)+0.0028×GPT (IU/L)

Discriminant Function Analysis:

Disease Score=1.1645×uPA (ng/ml)−2.4312×MMP9 (μg/ml)+0.0957×β-2MG (μg/ml)+0.0073×GPT (IU/L)+5

TABLE 16

Cutoff Values Representing Different Fibrosis Stage in a 3-Marker Ridge Regression Model

| | Training set(n = 145) | | | | Testing set(n = 84) | | | |
|---|---|---|---|---|---|---|---|---|
| Fibrosis Stage | F1~F4 | F2~F4 | F3~F4 | F4 | F1~F4 | F2~F4 | F3~F4 | F4 |
| Number of patients (%) | 82 (57%) | 72 (50%) | 50 (34%) | 30 (21%) | 54 (64%) | 44 (52%) | 36 (43%) | 20 (24%) |
| | Healthy vs. F1~F4 | Healthy, F1 vs. F2~F4 | Healthy, F1~F2 vs. F3, F4 | Healthy, F1~F3 vs. F4 | Healthy vs. F1~F4 | Healthy, F1 vs. F2~F4 | Healthy, F1~F2 vs. F3, F4 | Healthy, F1~F3 vs. F4 |
| Cutoff Value | 2.3896 | 2.5208 | 2.9041 | 3.1454 | 2.3896 | 2.5208 | 2.9041 | 3.1454 |
| Sensitivity (%) | 77 | 79 | 64 | 80 | 83 | 89 | 81 | 85 |
| Specificity (%) | 90 | 90 | 89 | 90 | 97 | 95 | 90 | 81 |
| Negative predictive value (%) | 75 | 81 | 83 | 94 | 76 | 88 | 86 | 95 |
| Positive predictive value (%) | 91 | 89 | 76 | 67 | 98 | 95 | 85 | 59 |
| Area under the ROC curve | 0.92 | 0.9 | 0.89 | 0.92 | 0.97 | 0.96 | 0.94 | 0.92 |

TABLE 17

Cutoff Values Representing Different Fibrosis Stage in a 4-Marker Discriminant Model

| | Training set (n = 145) | | | | Testing set (n = 84) | | | |
|---|---|---|---|---|---|---|---|---|
| Fibrosis Stage | F1~F4 | F2~F4 | F3~F4 | F4 | F1~F4 | F2~F4 | F3~F4 | F4 |
| Number of patients (%) | 82 (57%) | 72 (50%) | 50 (34%) | 30 (21%) | 54 (64%) | 44 (52%) | 36 (43%) | 20 (24%) |
| | Healthy vs. F1~F4 | Healthy, F1 vs. F2~F4 | Healthy, F1~F2 vs. F3~F4 | Healthy, F1~F3 vs. F4 | Healthy vs. F1~F4 | Healthy, F1 vs. F2~F4 | Healthy, F1~F2 vs. F3~F4 | Healthy, F1~F3 vs. F4 |
| Cutoff Value | 5.6290 | 5.7334 | 6.8026 | 6.9384 | 5.6290 | 5.7334 | 6.8026 | 6.9384 |
| Sensitivity (%) | 87 | 89 | 56 | 80 | 93 | 93 | 69 | 75 |
| Specificity (%) | 90 | 90 | 89 | 90 | 97 | 85 | 90 | 80 |
| NPV (%) | 84 | 89 | 79 | 94 | 88 | 92 | 80 | 91 |
| PPV (%) | 92 | 90 | 74 | 67 | 98 | 87 | 83 | 54 |
| AUROC | 0.96 | 0.93 | 0.9 | 0.91 | 0.99 | 0.96 | 0.91 | 0.87 |

The coefficient vales of uPA, MMP9, β-2MG, and GPT were 0.196 to 1.376 (e.g., 0.99 to 1.339), −6.684 to −1.623 (e.g., −2.796 to −2.067), 0.055 to 0.974 (e.g., 0.081 to 0.11), and 0.004 to 0.012 (e.g., 0.0062 to 0.0084), respectively.

Logistic Regression Analysis:

Disease Score=exp (Logit_value)/(1+exp (Logit_value)), in which

Logit_value=−3.6742+3.0107×uPA (ng/ml)−4.4549×MMP9 (μg/ml)+0.7074×β-2MG (μg/ml)+−0.0017×GPT (IU/L)

TABLE 18

Cutoff Values Representing Different Fibrosis Stage in a 4-Marker Logistic Regression Model

| | Training set (n = 145) | | | | Testing set (n = 84) | | | |
|---|---|---|---|---|---|---|---|---|
| Fibrosis Stage | F1~F4 | F2~F4 | F3~F4 | F4 | F1~F4 | F2~F4 | F3~F4 | F4 |
| Number of patients (%) | 82 (57%) | 72 (50%) | 50 (34%) | 30 (21%) | 54 (64%) | 44 (52%) | 36 (43%) | 20 (24%) |
| | Healthy vs. F1~F4 | Healthy, F1 vs. F2~F4 | Healthy, F1~F2 vs. F3~F4 | Healthy, F1~F3 vs. F4 | Healthy vs. F1~F4 | Healthy, F1 vs. F2~F4 | Healthy, F1~F2 vs. F3~F4 | Healthy, F1~F3 vs. F4 |
| Cutoff Value | 0.1905 | 0.2895 | 0.4522 | 0.5775 | 0.1905 | 0.2895 | 0.4522 | 0.5775 |
| Sensitivity (%) | 78 | 76 | 74 | 83 | 74 | 82 | 67 | 85 |
| Specificity (%) | 90 | 90 | 89 | 90 | 100 | 95 | 94 | 89 |
| NPV (%) | 76 | 80 | 87 | 95 | 68 | 83 | 79 | 95 |
| PPV (%) | 91 | 89 | 79 | 68 | 100 | 95 | 89 | 71 |
| AUROC | 0.92 | 0.92 | 0.92 | 0.94 | 0.98 | 0.96 | 0.95 | 0.95 |

The coefficient value of intercept was −4.74 to −2.61 (e.g., −4.225 to −3.123) and those of uPA, MMP9, β-2MG, and GPT were 2.24 to 3.77 (e.g., 2.559 to 3.462), −6.99 to −1.92 (e.g., −5.123 to −3.787), 0.39 to 1.02 (e.g., 0.6013 to 0.8135), and −0.004 to 0.001 (e.g., −0.002 to −0.001).

Ridge Regression Analysis:

Disease Score=1.2866+1.5874×uPA (ng/ml)−1.5725×MMP9 (μg/ml)+0.0955×β-2MG (μg/ml)+0.0029×GPT (IU/L)

TABLE 19

Cutoff Values Representing Different Fibrosis Stage in a 4-Marker Ridge Regression Model

| | Training set (n = 145) | | | | Testing set (n = 84) | | | |
|---|---|---|---|---|---|---|---|---|
| Fibrosis Stage | F1~F4 | F2~F4 | F3~F4 | F4 | F1~F4 | F2~F4 | F3~F4 | F4 |
| Number of patients (%) | 82 (57%) | 72 (50%) | 50 (34%) | 30 (21%) | 54 (64%) | 44 (52%) | 36 (43%) | 20 (24%) |

TABLE 19-continued

Cutoff Values Representing Different Fibrosis Stage in a 4-Marker Ridge Regression Model

| | Training set (n = 145) | | | | Testing set (n = 84) | | | |
|---|---|---|---|---|---|---|---|---|
| Fibrosis Stage | F1~F4 | F2~F4 | F3~F4 | F4 | F1~F4 | F2~F4 | F3~F4 | F4 |
| | Healthy vs. F1~F4 | Healthy, F1 vs. F2~F4 | Healthy, F1~F2 vs. F3~F4 | Healthy, F1~F3 vs. F4 | Healthy vs. F1~F4 | Healthy, F1 vs. F2~F4 | Healthy, F1~F2 vs. F3~F4 | Healthy, F1~F3 vs. F4 |
| Cutoff Value | 2.3499 | 2.5306 | 2.9141 | 3.0809 | 2.3499 | 2.5306 | 2.9141 | 3.0809 |
| Sensitivity (%) | 78 | 78 | 68 | 83 | 83 | 86 | 78 | 85 |
| Specificity (%) | 90 | 90 | 89 | 90 | 97 | 95 | 90 | 81 |
| NPV (%) | 76 | 80 | 84 | 95 | 76 | 86 | 84 | 95 |
| PPV (%) | 91 | 89 | 77 | 68 | 98 | 95 | 85 | 59 |
| AUROC | 0.93 | 0.91 | 0.9 | 0.93 | 0.98 | 0.96 | 0.95 | 0.92 |

The coefficient value of intercept was 0.297 to 2.109 (e.g., 1.094 to 1.48), and those of uPA, MMP9, β-2MG, and GPT were 0.748 to 1.800 (e.g., 1.349 to 1.778), −3.919 to −0.776 (e.g., −1.808 to −1.337), 0.077 to 0.830 (e.g., 0.0812 to 0.1098), and 0.001 to 0.007 (e.g., 0.0025 to 0.0033).

(vi) Five-Marker Models for Diagnosing Liver Fibrosis

The results obtained from this study indicate that combinations of any five factors of uPA, MMP9, β-2MG, GOT, GPT, AFP, taking into consideration clinical factors where applicable, are reliable markers for diagnosing liver fibrosis. Described below is an exemplary 5-marker model composed of uPA, MMP9, β-2MG, GPT, GOT. The results are shown in Tables 20-22.

Discriminant Function Analysis:

$$\text{Disease Score} = 1.1009 \times uPA\ (ng/\text{ml}) - 2.2941 \times MMP9\ (\mu g/\text{ml}) + 0.0974 \times \beta\text{-}2MG\ (\mu g/\text{ml}) + 0.0065 \times GPT\ (IU/L) + 0.0024 \times GOT(IU/L) + 5$$

TABLE 20

Cutoff Values Representing Different Fibrosis Stage in a 5-Marker Discriminant Model

| | Training set (n = 133) | | | | Testing set (n = 75) | | | |
|---|---|---|---|---|---|---|---|---|
| Fibrosis Stage | F1~F4 | F2~F4 | F3~F4 | F4 | F1~F4 | F2~F4 | F3~F4 | F4 |
| Number of patients (%) | 70 (53%) | 60 (45%) | 39 (29%) | 19 (14%) | 45 (60%) | 35 (47%) | 27 (36%) | 11 (15%) |
| | Healthy vs. F1~F4 | Healthy, F1 vs. F2~F4 | Healthy, F1~F2 vs. F3~F4 | Healthy, F1~F3 vs. F4 | Healthy vs. F1~F4 | Healthy, F1 vs. F2~F4 | Healthy, F1~F2 vs. F3~F4 | Healthy, F1~F3 vs. F4 |
| Cutoff Value | 5.6410 | 5.7987 | 6.9746 | 7.0015 | 5.6410 | 5.7987 | 6.9746 | 7.0015 |
| Sensitivity (%) | 86 | 87 | 46 | 74 | 93 | 91 | 63 | 73 |
| Specificity (%) | 90 | 90 | 90 | 90 | 97 | 85 | 92 | 81 |
| NPV (%) | 85 | 89 | 80 | 95 | 91 | 92 | 81 | 95 |
| PPV (%) | 91 | 88 | 67 | 56 | 98 | 84 | 81 | 40 |
| AUROC | 0.95 | 0.92 | 0.89 | 0.9 | 0.99 | 0.95 | 0.91 | 0.88 |

The coefficient values of uPA, MMP9, β-2MG, GPT, GOT were −0.070 to 1.512 (e.g., 0.936 to 1.266), −6.453 to −1.468 (e.g., −2.638 to −1.95), 0.058 to 1.209 (e.g., 0.083 to 0.112), −0.002 to 0.019 (e.g., 0.0055 to 0.0075), and −0.011 to 0.025 (e.g., 0.002 to 0.0028), respectively.

Logistic Regression Analysis:

Disease Score=exp (Logit_value)/(1+exp (Logit_value)), in which

Logit_value=−3.4751+2.7416×uPA (ng/ml)−4.5237× MMP9 (µg/ml)+0.6952×β-2MG (µg/ml)−0.0021×GPT (IU/L)+0.0007×GOT (IU/L)

The coefficient value of intercept comprised was 0.145 to 1.909 (e.g., 1.084 to 1.466) and those of uPA, MMP9, β-2MG, GPT, and GOT were 0.576 to 1.826 (e.g., 1.148 to 1.553), −3.676 to −0.603 (e.g., −1.65 to −1.219), 0.077 to 0.862 (e.g., 0.0831 to 0.1125), −0.005 to 0.009 (e.g., 0.0003 to 0.0004), and −0.008 to 0.021 (e.g., 0.0047 to 0.0065), respectively.

(vii) Six-Marker Models for Diagnosing Liver Fibrosis

The results obtained from this study indicate that a combination of uPA, MMP9, β-2MG, GOT, GPT, and AFP,

TABLE 21

Cutoff Values Representing Different Fibrosis Stage in a 5-Marker Logistic Regression Model

| | Training set (n = 133) | | | | Testing set (n = 75) | | | |
|---|---|---|---|---|---|---|---|---|
| Fibrosis Stage | F1~F4 | F2~F4 | F3~F4 | F4 | F1~F4 | F2~F4 | F3~F4 | F4 |
| Number of patients (%) | 70 (53%) | 60 (45%) | 39 (29%) | 19 (14%) | 45 (60%) | 35 (47%) | 27 (36%) | 11 (15%) |
| | Healthy vs. F1~F4 | Healthy, F1 vs. F2~F4 | Healthy, F1~F2 vs. F3~F4 | Healthy, F1~F3 vs. F4 | Healthy vs. F1~F4 | Healthy, F1 vs. F2~F4 | Healthy, F1~F2 vs. F3~F4 | Healthy, F1~F3 vs. F4 |
| Cutoff Value | 0.1948 | 0.2854 | 0.4667 | 0.5551 | 0.1948 | 0.2854 | 0.4667 | 0.5551 |
| Sensitivity (%) | 74 | 72 | 64 | 79 | 69 | 77 | 59 | 82 |
| Specificity (%) | 90 | 90 | 90 | 90 | 100 | 95 | 94 | 89 |
| NPV (%) | 76 | 80 | 86 | 96 | 68 | 83 | 80 | 97 |
| PPV (%) | 90 | 86 | 74 | 58 | 100 | 93 | 84 | 56 |
| AUROC | 0.91 | 0.91 | 0.9 | 0.91 | 0.98 | 0.95 | 0.94 | 0.93 |

The coefficient value of intercept was −4.54 to −2.4 (e.g., −3.996 to −2.954) and those of uPA, MMP9, β-2MG, GPT, and GOT were 1.87 to 3.61 (e.g., 2.33 to 3.153), −7.13 to −1.9 (e.g., −5.202 to −3.845), 0.38 to 1.01 (e.g., 0.5909 to 0.7995), −0.01 to 0.01 (e.g., −0.0024 to −0.0018), and −0.01 to 0.01 (e.g., 0.0006 to 0.0008), respectively.

Ridge Regression Analysis:

Disease Score=1.2750+1.3505×uPA (ng/ml)−1.4346× MMP9 (µg/ml)+0.0978×β-2MG (µg/ml)+0.0004×GPT (IU/L)+0.0056×GOT (IU/L)

taking into account clinical factors when necessary, is a reliable marker for diagnosing liver fibrosis. Shown below are equations for calculating disease scores (established by discriminant analysis, logistic regression analysis, and ridge regression analysis) based on this 6-marker combinations and cutoff values for different fibrosis stages (see Tables 23-25 below).

TABLE 22

Cutoff Values Representing Different Fibrosis Stage in a 5-Marker Ridge Regression Model

| | Training set (n = 133) | | | | Testing set (n = 75) | | | |
|---|---|---|---|---|---|---|---|---|
| Fibrosis Stage | F1~F4 | F2~F4 | F3~F4 | F4 | F1~F4 | F2~F4 | F3~F4 | F4 |
| Number of patients (%) | 70 (53%) | 60 (45%) | 39 (29%) | 19 (14%) | 45 (60%) | 35 (47%) | 27 (36%) | 11 (15%) |
| | Healthy vs. F1~F4 | Healthy, F1 vs. F2~F4 | Healthy, F1~F2 vs. F3~F4 | Healthy, F1~F3 vs. F4 | Healthy vs. F1~F4 | Healthy, F1 vs. F2~F4 | Healthy, F1~F2 vs. F3~F4 | Healthy, F1~F3 vs. F4 |
| Cutoff Value | 2.2006 | 2.3922 | 2.9473 | 3.1712 | 2.2006 | 2.3922 | 2.9473 | 3.1712 |
| Sensitivity (%) | 79 | 77 | 54 | 79 | 87 | 91 | 70 | 82 |
| Specificity (%) | 90 | 90 | 90 | 90 | 97 | 93 | 94 | 81 |
| NPV (%) | 79 | 82 | 83 | 96 | 83 | 93 | 85 | 96 |
| PPV (%) | 90 | 87 | 70 | 58 | 98 | 91 | 86 | 43 |
| AUROC | 0.93 | 0.91 | 0.89 | 0.91 | 0.98 | 0.96 | 0.94 | 0.91 |

Discriminant Function Analysis:

$$\text{Disease Score} = 1.4401 \times uPA\ (ng/ml) - 1.2831 \times MMP9\ (\mu g/ml) +$$
$$0.0921 \times \beta\text{-}2MG\ (\mu g/ml) - 0.0099 \times AFP\ (ng/ml) +$$
$$0.0129 \times GPT\ (IU/L) - 0.0004 \times GOT(IU/L) + 5$$

TABLE 23

Cutoff Values Representing Different Fibrosis Stage in a 6-Marker Discriminant Model

| | Training set (n = 109) | | | | Testing set (n = 53) | | | |
|---|---|---|---|---|---|---|---|---|
| Fibrosis Stage | F1~F4 | F2~F4 | F3~F4 | F4 | F1~F4 | F2~F4 | F3~F4 | F4 |
| Number of patients (%) | 46 46(%) | 39 (36%) | 27 (25%) | 16 (15%) | 24 (45%) | 18 (34%) | 14 (26%) | 11 (21%) |
| | Healthy vs. F1~F4 | Healthy, F1 vs. F2~F4 | Healthy, F1~F2 vs. F3~F4 | Healthy, F1~F3 vs. F4 | Healthy vs. F1~F4 | Healthy, F1 vs. F2~F4 | Healthy, F1~F2 vs. F3~F4 | Healthy, F1~F3 vs. F4 |
| Cutoff Value | 6.1727 | 6.3100 | 6.6171 | 7.7270 | 6.1727 | 6.3100 | 6.6171 | 7.7270 |
| Sensitivity (%) | 89 | 82 | 81 | 75 | 88 | 94 | 86 | 73 |
| Specificity (%) | 90 | 90 | 90 | 90 | 93 | 91 | 87 | 86 |
| NPV (%) | 92 | 90 | 94 | 95 | 90 | 97 | 94 | 92 |
| PPV (%) | 87 | 82 | 73 | 57 | 91 | 85 | 71 | 57 |
| AUROC | 0.94 | 0.9 | 0.91 | 0.9 | 0.98 | 0.96 | 0.91 | 0.89 |

The coefficient values of uPA, MMP9, β-2MG, AFP, GPT, and GOT were 0.141 to 1.923 (e.g., 1.224 to 1.656), −5.052 to −0.393 (e.g., −1.476 to −1.091), 0.069 to 1.303 (e.g., 0.078 to 0.106), −0.032 to 0.054 (e.g., −0.0114 to −0.0084), 0.002 to 0.032 (e.g., 0.011 to 0.0148), and −0.023 to 0.021 (e.g., −0.00046 to −0.00034), respectively.

Logistic Regression Analysis:

Disease Score=exp (Logit_value)/(1+exp (Logit_value)), in which

Logit_value=−4.1023+2.4436×uPA (ng/ml)−6.8921× MMP9 (µg/ml)+1.2869×β-2MG (µg/ml)−0.0112×AFP (ng/ml)−0.0015×GPT (IU/L)+0.0018×GOT (IU/L)

The coefficient value of intercept was −5.6 to −2.61 (e.g., −4.718 to −3.487) and those of uPA, MMP9, β-2MG, GPT, GOT, and AFP were 1.38 to 3.5 (e.g., 2.077 to 2.81), −10.86 to −2.92 (e.g., −7.926 to −5.858), 0.82 to 1.75 (e.g., 1.0939 to 1.4799), −0.01 to 0.01 (e.g., −0.0017 to −0.0012), −0.01 to 0.01 (e.g., 0.0015 to 0.002), and −0.01 to 0.02 (e.g., −0.01 to −0.0095), respectively.

Ridge Regression Analysis:

Disease Score=0.9632+1.4215×uPA (ng/ml)−1.0722× MMP9 (µg/ml)+0.0986×β-2MG (µg/ml)−0.0053×AFP (ng/ml)+0.0019×GPT (IU/L)+0.0058×GOT (IU/L)

TABLE 24

Cutoff Values Representing Different Fibrosis Stage in a 6-Marker Logistic Regression Model

| | Training set (n = 109) | | | | Testing set (n = 53) | | | |
|---|---|---|---|---|---|---|---|---|
| Fibrosis Stage | F1~F4 | F2~F4 | F3~F4 | F4 | F1~F4 | F2~F4 | F3~F4 | F4 |
| Number of patients (%) | 46 46(%) | 39 (36%) | 27 (25%) | 16 (15%) | 24 (45%) | 18 (34%) | 14 (26%) | 11 (21%) |
| | Healthy vs. F1~F4 | Healthy, F1 vs. F2~F4 | Healthy, F1~F2 vs. F3~F4 | Healthy, F1~F3 vs. F4 | Healthy vs. F1~F4 | Healthy, F1 vs. F2~F4 | Healthy, F1~F2 vs. F3~F4 | Healthy, F1~F3 vs. F4 |
| Cutoff Value | 0.1569 | 0.1617 | 0.3392 | 0.5628 | 0.1569 | 0.1617 | 0.3392 | 0.5628 |
| Sensitivity (%) | 74 | 82 | 81 | 75 | 67 | 89 | 86 | 91 |
| Specificity (%) | 90 | 90 | 90 | 90 | 100 | 100 | 95 | 98 |
| NPV (%) | 83 | 90 | 94 | 95 | 78 | 95 | 95 | 91 |
| PPV (%) | 85 | 82 | 73 | 57 | 100 | 100 | 86 | 98 |
| AUROC | 0.91 | 0.93 | 0.94 | 0.93 | 0.99 | 1 | 0.99 | 0.98 |

TABLE 25

Cutoff Values Representing Different Fibrosis Stage in a 6-Marker Ridge Regression Model

| Fibrosis Stage | Training set(n = 109) | | | | Testing set(n = 53) | | | |
|---|---|---|---|---|---|---|---|---|
| | F1~F4 | F2~F4 | F3~F4 | F4 | F1~F4 | F2~F4 | F3~F4 | F4 |
| Number of patients (%) | 46 46(%) | 39 (36%) | 27 (25%) | 16 (15%) | 24 (45%) | 18 (34%) | 14 (26%) | 11 (21%) |
| | Healthy vs. F1~F4 | Healthy, F1 vs. F2~F4 | Healthy, F1~F2 vs. F3~F4 | Healthy, F1~F3 vs. F4 | Healthy vs. F1~F4 | Healthy, F1 vs. F2~F4 | Healthy, F1~F2 vs. F3~F4 | Healthy, F1~F3 vs. F4 |
| Cutoff Value | 2.0424 | 2.1525 | 2.5894 | 2.9761 | 2.0424 | 2.1525 | 2.5894 | 2.9761 |
| Sensitivity (%) | 76 | 82 | 70 | 81 | 83 | 100 | 93 | 73 |
| Specificity (%) | 90 | 90 | 90 | 90 | 93 | 94 | 87 | 93 |
| NPV (%) | 84 | 90 | 90 | 97 | 87 | 100 | 97 | 93 |
| PPV (%) | 85 | 82 | 70 | 59 | 91 | 90 | 72 | 73 |
| AUROC | 0.92 | 0.91 | 0.92 | 0.91 | 0.99 | 0.99 | 0.96 | 0.95 |

The coefficient value of intercept was −0.336 to 1.587 (e.g., 0.819 to 1.108) and those of uPA, MMP9, β-2MG, AFP, GPT, and GOT were 0.396 to 2.024 (e.g., 1.208 to 1.635), −2.763 to −0.256 (e.g., −1.239 to −0.916), 0.087 to 1.034 (e.g., 0.088 to 0.113), −0.021 to 0.037 (e.g., −0.0061 to −0.0045), −0.006 to 0.015 (e.g., 0.0016 to 0.0021), and −0.014 to 0.024 (e.g., 0.0049 to 0.0066), respectively.

All of the above mentioned models were validated in the test set and similar results, including cutoff values, sensitivity, specificity, NPV, PPV, and AUROC, were observed.

EXAMPLE 2

Diagnosing Liver Fibrosis in HBV-Positive Patients Based on Serum Levels of uPA, MMP9, and β-2MG The single- and 3-marker models were also validated in 30 patients carrying HBV and 30 healthy subjects in this study. Table 26 below lists characteristics of this data set.

TABLE 26

Patient Characteristics

| | Data set (n = 60) |
|---|---|
| Age, mean (SD) | 44.23 (9.27) |
| Female, n (%) | 17 (28%) |
| Serum Biochemical Makers, mean (SD) | |
| GOT/AST, IU/L | 54.53 (59.56) |
| GPT/ALT, IU/L | 87.02 (129.47) |
| T. Bilirubin, μmol/L | 21.52 (21.78 |
| Albumin, g/L | 42.3 (5.88) |
| AFP, ng/ml | 8.73 (26.62) |
| Novel Serum Markers, mean (SD) | |
| uPA, ng/ml | 0.73 (0.6) |
| MMP9, μg/ml | 0.27 (0.22) |
| β-2MG, μg/ml | 1.44 (1.16) |

As shown in Table 27 below, the serum level of each of uPA, MMP9, and β-2MG correlates with fibrosis severity:

TABLE 27

Serum Levels of uPA, MMP9, and β-2MG in HBV-Positive Patients

| | uPA (ng/ml) | MMP9 (μg/ml) | β-2MG (μg/ml) |
|---|---|---|---|
| Healthy (n = 30) | 0.46 (0.18) | 0.4 (0.23) | 1.1 (0.18) |
| F1 (n = 9) | 0.87 (0.53) | 0.18 (0.04) | 1.17 (0.4) |
| F2 (n = 3) | 0.42 (0.1) | 0.08 (0.01) | 1.13 (0.26) |
| F3 (n = 7) | 0.77 (0.35) | 0.13 (0.06) | 1.42 (0.42) |
| F4 (n = 11) | 1.45 (0.93) | 0.11 (0.05) | 2.68 (2.34) |

*Number of healthy: 30 subjects (testing set);

The cutoff values representing different fibrosis stages based on disease scores calculated following the equations described in the 3-Marker model in Example 1 above were shown in Tables 28-30 below (the healthy test set mentioned above was subjected to this study):

TABLE 28

Cutoff Values Representing Different Fibrosis Stage in a 3-Marker Discriminant Model for HBV-Positive Patients

| | Data set (n = 60) | | | |
|---|---|---|---|---|
| Fibrosis Stage | F1~F4 | F2~F4 | F3~F4 | F4 |
| Number of patients (%) | 30 (50%) | 21 (35%) | 18 (30%) | 11 (18%) |
| | Healthy vs. F1~F4 | Healthy, F1 vs. F2~F4 | Healthy, F1~F2 vs. F3, F4 | Healthy, F1~F3 vs. F4 |
| Cutoff Value | 5.5918 | 5.7362 | 6.0726 | 6.2124 |
| Sensitivity (%) | 53 | 57 | 56 | 64 |
| Specificity (%) | 97 | 92 | 95 | 92 |
| NPV (%) | 67 | 80 | 83 | 92 |
| PPV (%) | 94 | 80 | 83 | 64 |
| AUROC | 0.96 | 0.89 | 0.89 | 0.88 |

TABLE 29

Cutoff Values Representing Different Fibrosis Stage in a 3-Marker Logistic Regression Model for HBV-Positive Patients

| | Data set (n = 60) | | | |
|---|---|---|---|---|
| Fibrosis Stage | F1~F4 | F2~F4 | F3~F4 | F4 |
| Number of patients (%) | 30 (50%) | 21 (35%) | 18 (30%) | 11 (18%) |
| | Healthy vs. F1~F4 | Healthy, F1 vs. F2~F4 | Healthy, F1~F2 vs. F3, F4 | Healthy, F1~F3 vs. F4 |
| Cutoff Value | 0.1962 | 0.2806 | 0.4863 | 0.5961 |
| Sensitivity (%) | 57 | 52 | 50 | 64 |
| Specificity (%) | 100 | 95 | 95 | 96 |
| NPV (%) | 70 | 79 | 82 | 92 |
| PPV (%) | 100 | 85 | 82 | 78 |
| AUROC | 0.95 | 0.88 | 0.89 | 0.88 |

TABLE 30

Cutoff Values Representing Different Fibrosis Stage in a 3-Marker Ridge Regression Model for HBV-Positive Patients

| | Data set (n = 60) | | | |
|---|---|---|---|---|
| Fibrosis Stage | F1~F4 | F2~F4 | F3~F4 | F4 |
| Number of patients (%) | 30 (50%) | 21 (35%) | 18 (30%) | 11 (18%) |
| | Healthy vs. F1~F4 | Healthy, F1 vs. F2~F4 | Healthy, F1~F2 vs. F3, F4 | Healthy, F1~F3 vs. F4 |
| Cutoff Value | 2.0620 | 2.4571 | 2.4571 | 2.7726 |
| Sensitivity (%) | 90 | 57 | 67 | 73 |
| Specificity (%) | 90 | 90 | 90 | 90 |
| NPV (%) | 90 | 80 | 86 | 94 |
| PPV (%) | 90 | 75 | 75 | 62 |
| AUROC | 0.94 | 0.85 | 0.88 | 0.86 |

EXAMPLE 3

Diagnosing Liver Fibrosis in Patients Having Alcohol-Related Liver Disease Based on Serum Levels of uPA, MMP9, and β-2MG 53 patients having alcohol-related liver diseases and 30 healthy subjects participated in this study. The patient characteristics are listed in Table 31 below. These patients were subjected to routine laboratory tests as described in Example 1 above and also modified Skinner survey to determine their alcohol consumption habit.

TABLE 31

Patient Characteristics

| | Data set (n = 83) |
|---|---|
| Age, mean (SD) | 43.83 (9.23) |
| Female, n (%) | 15 (18%) |
| Serum Biochemical Makers, mean (SD) | |
| GOT/AST, IU/L | 67.88 (71.87) |
| GPT/ALT, IU/L | 46.28 (57.22) |
| T. Bilirubin, µmol/L | 53.31 (50.8) |
| Albumin, g/L | 35.02 (7.15) |
| AFP, ng/ml | 103.81 (892.5) |
| Novel Serum Markers, mean (SD) | |
| uPA, ng/ml | 1.11 (1.07) |
| MMP9, µg/ml | 0.3 (0.24) |
| β-2MG, µg/ml | 1.77 (1.11) |

Serum levels of uPA, MMP9, and β-2MG in these patients were examined following the ELISA assays described in Example 1. The results thus obtained are shown below Table 32.

TABLE 32

Serum Levels of uPA, MMP9, and β-2MG in Patients Suffering from Alcohol-Related Disease

| | uPA (ng/ml) | MMP9 (µg/ml) | β-2MG (µg/ml) |
|---|---|---|---|
| Healthy (n = 30) | 0.46 (0.18) | 0.4 (0.23) | 1.1 (0.18) |
| Fatty Liver (n = 15) | 0.57 (0.27) | 0.37 (0.28) | 1.84 (0.84) |
| Hepatitis (n = 7) | 1.12 (0.93) | 0.27 (0.19) | 1.91 (0.66) |
| F4 (n = 31) | 2 (1.23) | 0.17 (0.17) | 2.36 (1.45) |

Disease scores of these patients were calculated following the 3-marker equation described in Example 1 above and cutoff values for different fibrosis stages are shown in Table 33 below:

TABLE 33

Cutoff Values Representing Different Fibrosis Stage in a 3-Marker Model for Patients Having Alcohol-Related Disease

| | Data set (n = 83) | | |
|---|---|---|---|
| | Discriminant model | Logistic regression model | Ridge regression model |
| Fibrosis Stage | | F4 | |
| Number of patients (%) | 31 (37%) | 31 (37%) | 31 (37%) |
| | Healthy, Fatty_liver, Alcoholic_Hepatitis vs. F4 | | |
| Cutoff Value | 5.6430 | 0.2606 | 2.5453 |
| Sensitivity (%) | 90 | 90 | 94 |
| Specificity (%) | 90 | 90 | 90 |
| NPV (%) | 94 | 94 | 96 |
| PPV (%) | 85 | 85 | 85 |
| AUROC | 0.93 | 0.94 | 0.95 |

*Number of healthy: 30 subjects (testing set);
Number of Fatty_liver and Alcoholic_Hepatitis: 22 subjects

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A non-invasive method for detecting and discriminating stages of liver fibrosis in a hepatitis C virus (HCV)-positive human subject, the method comprising:

obtaining a blood sample from a HCV-positive human subject;

assaying the blood sample, with an immune assay, to detect and measure in the sample three protein levels consisting essentially of a urokinase-type plasminogen activator (uPA) protein level, a matrix metalloproteinase 9 (MMP9) protein level, and a β-2-microglobulin (β-2MG) protein level;

determining a relationship among the three protein levels in the sample to detect and stage liver fibrosis in the subject, wherein the relationship is (i) A=[1.4159×uPA (ng/ml)]−[3.0399×MMP9 (µg/ml)]+[0.0897×β-2MG (µg/ml)]+5; (ii) B=0.09 exp (Logit_value)/(1+exp (Logit_value)), in which Logit_value=−3.8614+[2.8761×uPA (ng/ml)]−[4.0100×MMP9 (µg/ml)]+[0.7853×β-2MG (µg/ml)]; or (iii) C=1.4645+[1.6683×uPA (ng/ml)]−[1.7868×MMP9 (µg/ml)]+[0.0926×β-2MG (µg/ml)], and wherein (a) the subject is diagnosed to be free of liver fibrosis if A is less than or equal to 5.21, B is less than or equal to 0.09, or C is less than or equal to 2.00;
(b) the subject is diagnosed to be free of liver fibrosis or have stage F1 liver fibrosis if A is less than 5.26, B is less than 0.11, or C is less than 2.05;
(c) the subject is diagnosed to have stage F1 liver fibrosis if A is less than or equal to 5.55, B is less than or equal to 0.28, or C is less than or equal to 2.40;
(d) the subject is diagnosed to have stage F1 or stage F2 liver fibrosis if A is less than 5.63, B is less than 0.35, or C is less than 2.50;
(e) the subject is diagnosed to have stage F2 liver fibrosis if A is less than or equal to 6.01, B is less than or equal to 0.5, or C is less than or equal to 2.90;
(f) the subject is diagnosed to have stage F2 or stage F3 liver fibrosis if A is less than 6.10, B is less than 0.54, or C is less than 3.00;
(g) the subject is diagnosed to have stage F3 liver fibrosis if A is less than or equal to 6.62, B is less than or equal to 0.75, or C is less than or equal to 3.8;
(h) the subject is diagnosed to have stage F3 or stage F4 liver fibrosis if A is less than 6.78, B is less than 0.85, or C is less than 3.90; and
(i) the subject is diagnosed to have stage F4 liver fibrosis if A is greater than or equal to 6.78, B is greater than or equal to 0.85, or C is greater than or equal to 3.9.

2. A non-invasive method for detecting and discriminating stages of liver fibrosis in a hepatitis B virus (HBV)-positive human subject, the method comprising:

obtaining a blood sample from a HBV-positive human subject;

assaying the blood sample, with an immune assay, to detect and measure in the sample three protein levels consisting essentially of a urokinase-type plasminogen activator (uPA) protein level, a matrix metalloproteinase 9 (MMP9) protein level, and a β-2-microglobulin (β-2MG) protein level;

determining a relationship among the three protein levels in the sample to detect and stage liver fibrosis in the subject, wherein the relationship is (i) A=[1.4159×uPA (ng/ml)]−[3.0399×MMP9 (µg/ml)]+[0.0897×β-2MG (µg/ml)]+5; (ii) B=0.09 exp (Logit_value)/(1+exp (Logit_value)), in which Logit_value=−3.8614+[2.8761×uPA (ng/ml)]−[4.0100×MMP9 (µg/ml)]+[0.7853×β-2MG (µg/ml)]; or (iii) C=1.4645+[1.6683×uPA (ng/ml)]−[1.7868×MMP9 (µg/ml)]+[0.0926×β-2MG (µg/ml)], and wherein (a) The subject is diagnosed to be free of liver fibrosis if A is less than or equal to 5.5918, B is less than or equal to 0.1962, or C is less than or equal to 2.0620;
(b) The subject is diagnosed to be free of liver fibrosis or have stage F1 liver fibrosis if A is less than or equal to 5.7362, B is less than or equal to 0.2806, or C is less than or equal to 2.4571;
(c) The subject is diagnosed to be free of liver fibrosis, or have F1 or F2 liver fibrosis if A is less than or equal to 6.0726, B is less than or equal to 0.4863, or C is less than or equal to 2.4571;
(d) The subject is diagnosed to be free of liver fibrosis, or have F1, F2 or F3 liver fibrosis if A is less than or equal to 6.2124, B is less than or equal to 0.5961, or C is less than or equal to 2.7726; and
(e) The subject is diagnosed to have stage F4 liver fibrosis if A is greater than 6.2124, B is greater than 0.5961, or C is greater than 2.7726.

* * * * *